United States Patent [19]

Marshall et al.

[11] Patent Number: 4,777,298

[45] Date of Patent: Oct. 11, 1988

[54] PROCESS FOR INTERMEDIATES TO LEUKOTRIENE ANTAGONISTS

[75] Inventors: Winston S. Marshall, Bargersville; Sandra K. Sigmund, Indianapolis; Celia A. Whitesitt, Greenwood, all of Ind.

[73] Assignee: Eli Lilly and Company, Indianapolis, Ind.

[21] Appl. No.: 142,118

[22] Filed: Jan. 11, 1988

Related U.S. Application Data

[63] Continuation of Ser. No. 064,897, Jun. 19, 1987, abandoned.

[51] Int. Cl.$^4$ ............................................. C07C 45/45
[52] U.S. Cl. ................................................... 568/319
[58] Field of Search ........................................ 508/319

[56] References Cited

U.S. PATENT DOCUMENTS 4,661,505  4/1987  Marshall et al. ..................... 568/319

FOREIGN PATENT DOCUMENTS 59-65039  4/1984  Japan ................................... 568/319

OTHER PUBLICATIONS

P. Da Re and L. Cimatoribus, *Journal of Organic Chemistry*, 26, pp. 3650–3653 (1961).
G. P. Schiemenz and U. Schmidt, *Liebigs Annalen der Chemie*, pp. 1514–1519, (1976).
J. March, *Advanced Organic Chemistry–Reactions, Mechanism, and Structure*, Second Edition, McGraw-Hill Book Company, New York, pp. 394–395 (1977).

*Primary Examiner*—James H. Reamer
*Attorney, Agent, or Firm*—Robert A. Conrad; Leroy Whitaker

[57] ABSTRACT

Resorcinol is acylated in a mixture of acetic or propionic acid and hydrobromic acid. The dihydroxy acylbenzenes thus produced are intermediates in the synthesis of leukotriene antagonists.

4 Claims, No Drawings

PROCESS FOR INTERMEDIATES TO LEUKOTRIENE ANTAGONISTS

This application is a continuation, of application Ser. No. 07/064,897, filed June 19, 1987 now abandoned.

BACKGROUND OF THE INVENTION

Dihydroxy acylbenzenes of the Formula A

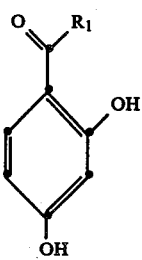

are important intermediates in the synthesis of leukotriene antagonist compounds, especially compounds of Formula B

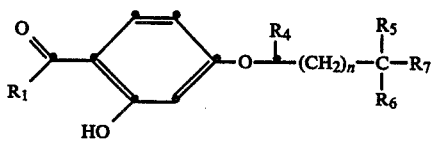

The compounds of Formula B are the subject of Marshall et al., U.S. Pat. No. 4,661,505, issued Apr. 28, 1987. The compounds of Formula B treat allergic disorders such as asthma, where leukotrienes are thought to be the causal mediators.

In the past, the phenones of Formula A have been prepared under Friedel-Crafts conditions.

Quite unexpectedly, we have found conditions to do the acylation reaction with cheap, commercially available reagents that are easier to handle than the traditional acid chloride and acid anhydride reagents. Furthermore, the conditions are such that there is no need to use (and thus properly dispose of it) the Lewis acid catalyst. The instant process simplifies the synthesis and thus lowers the cost of leukotriene antagonists such as those of the above Formula B. Thus, the benzene substrate was acylated with an acid chloride or anhydride and a Lewis acid (e.g. aluminum trichloride, iron (III) trichloride, zinc dichloride, boron trifluoride, anhydrous hydrogen fluoride). These Friedel-Crafts conditions created two problems, (especially on an industrial scale): (1) acid chlorides and acid anhydrides degrade to unreactive or less reactive reagents without the exclusion of water; and (2) many of the Friedel-Crafts catalysts (for example, hydrofluoric acid, aluminum trichloride, iron trichloride, etc.) were difficult to dispose of in an environmentally acceptable manner.

SUMMARY OF THE INVENTION

The invention is directed to a process for preparing 1,3-dihydroxy-4-(acetyl- or propionyl)benzene ("phenone") which comprises combining resorcinol (1,3-dihydroxybenzene) with a) acetic acid or propionic acid, respectively ("carboxylic acid"), and (b) hydrobromic acid at a temperature between about the boiling point of the reaction mixture to about 75° C. for between about one hour to about five days.

DETAILED DESCRIPTION OF THE INVENTION

The instant invention is directed to a process for preparing 1,3-(dihydroxy)-4-(acetyl or propionyl)-benzene which comprises combining resorcinol a) acetic acid or propionic acid, respectively, and b) hydrobromic acid at a temperature between about the boiling temperature of the reaction mixture to about 75° C. for between about one hour to about five days.

The stoichiometry of the above reaction is not critical. It is preferred that at least about one equivalent of the carboxylic acid reagent per equivalent of the resorcinol be present, with an excess of the carboxylic acid preferred. The hydrobromic acid can be present in only a catalytic amount, although an equimolar or an excess amount in relation to the resorcinol is preferred. When the carboxylic acid reagent is acetic acid, several commercial preparations are available, the most convenient for use in the process being glacial acetic acid. Propionic acid can be obtained commercially as a 99% solution, which can be used as is or diluted with water before using in the process.

Similarly, the hydrobromic acid reagent for the process may be conveniently supplied by the commercial preparation of 48% hydrobromic acid in water. However, aqueous solutions containing as little as 10% to saturated aqueous solutions of hydrobromic acid can be made in the conventional manner and used in the process. Alternatively, hydrogen bromide gas can be bubbled through the acetic acid or propionic acid to give the appropriate mixture of the two acids. In a preferred embodiment anhydrous hydrogen bromide gas is bubbled through excess glacial acetic acid or 99% propionic acid until the desired concentration of HBr is obtained.

The order of addition of resorcinol and carboxylic acid starting materials and the hydrobromic acid are not critical. Typically, resorcinol is dissolved in the carboxylic acid then the hydrobromic acid is added. Also, previously-prepared hydrogen bromide in acetic acid solution can be added to the resorcinol substrate.

The progress of the process is dependent on the concentration of the two acids and the temperature of the reaction mixture. The higher the concentration of acids, the faster the reaction proceeds. The progress can be monitored in the usual chromatographic and spectroscopic ways - such as by analyzing aliquots of the reaction mixture by nuclear magnetic resonance spectroscopy, thin layer chromatography, column chromatography, gas chromatography, or high pressure liquid chromatography. For instance, a small aliquot (e.g., 0.10 ml) can be withdrawn at an appropriate time, partitioned between water and ether, and the ether layer evaporated (the ether layer may additionally be washed with brine and dried over sodium or magnesium sulfate). The resultant residue can then be analyzed for presence of starting material and desired product by the analytical method of choice.

The time period for the process is most dependent on the concentration of the carboxylic and hydrobromic acids. The time period is from between about one hour to about 5 days, with approximately 4 to 48 hours typical. Higher yields and shorter reaction times are obtained when excess amounts of both the carboxylic acid and hydrobromic acid in relation to resorcinol are used.

Also, the best conditions for the reaction include those wherein the mixture of acids is anhydrous. For example, hydrogen bromide gas can be bubbled through glacial acetic acid prior to the reaction to obtain the appropriate mixture of acids. The temperature is not as critical as a factor in the time required for the process. The temperature should be from between about the boiling point of the reaction mixture (typically 100°–110° C.) to about 75° C.

The acylbenzene product of the instant process is isolated by conventional methods. For instance the reaction mixture can be extracted with an ether/water mixture. The ether layer can be further treated with brine and a suitable solid drying agent (such as sodium or magnesium sulfate) then concentrated to a residue. Alternately, the ether level could immediately be concentrated to a foam. The product can be used as is from this isolation, or can be purified by chromatographic techniques. A typical chromatographic procedure uses high pressure liquid chromatography on a silica gel column eluted with a gradient of 5 to 15% of ethyl acetate in hexane. Another typical chromatography technique is flash chromatography, where the crude reaction mixture concentrate is separated on a Kieselgel 60 support eluted with a gradient elution of from 1 to 5% ethyl acetate in hexane. The product-containing fractions can then be combined and concentrated.

There are several preferred embodiments of the instant process. The broadest of these occurs when 1,3-(dihydroxy)-4-acetylbenzene is produced with acetic acid. A more preferred embodiment occurs when the temperature is from between about 80° C. to about 90° C., and the most preferred occurs when the reaction mixture contains hydrogen bromide gas that has been dissolved in glacial acetic acid.

As discussed above, the products of the present process are starting materials for the synthesis of leukotriene antagonists. The products are especially useful for the synthesis of leukotriene antagonists of the above Formula B, which compounds are discussed in W. S. Marshall et al., U.S. Pat. No. 4,661,505, issued Apr. 28, 1987, herein incorporated by reference. The products of the present process are alkylated on the 1-hydroxy group with a compound of the formula

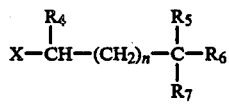

as discussed in columns 3 and 4 of the Marshall et al. patent.

As discussed above, the carboxylic acid reagents, the hydrobromic acid catalyst and the resorcinol substrate for the process are either commercially available or at least their preparation is well known in the art.

The following Examples are provided to further illustrate the instant invention. The Examples are for the benefit of those skilled in the art and are not to limit the scope of the invention in any way. Abbreviations used in the Examples are standard ones well known in the art; thus "HPLC" and "n.m.r" stand for high pressure liquid chromatography and nuclear magnetic resonance, respectively. The n.m.r. data reported below were obtained on a General Electric QE-300 300 MHz instrument in CDCl₃. The chemical shifts are referenced to TMS. In describing the n.m.r. spectra, "s" stands for singlet, "d" means a doublet, "t" means a triplet and "m" signifies a multiplet.

EXAMPLE 1

1,3-Dihydroxy-4-acetylbenzene

Resorcinol (0.55 g, 5.0 mmol) was dissolved in 5% hydrobromic acid in glacial acetic acid (155 ml, made by bubbling hydrogen bromide gas through glacial acetic acid). The reaction mixture was heated to 80° C. for 4.5 hours. The reaction solution was cooled to room temperature, added to water (500 ml) and the aqueous solution was extracted with ether (500 ml, 2X). The ether phases combined and washed with brine (100 ml), dried over magnesium sulfate, filtered and evaporated to dryness in vacuo. The residue was recrystallized from an ether/hexane mixture to give 0.40 g, 53% of the title product:

n.m.r.: δ 12.70 (s, 1H), 7.64 (d, 1H), 6.40 (d, 1H), 6.38, (s, 1H), 2.57 (s, 3H).

EXAMPLE 2

1,3-Dihydroxy-4-acetylbenzene

In a procedure similar to Example 1, resorcinol (0.55 g, 5.0 mmol) was dissolved in 20% hydrogen bromide in glacial acetic acid (40 g, 99 mmol of HBr, made by bubbling hydrogen bromide gas through glacial acetic acid) and the mixture was heated to 80° C. for 5.5 hours. Isolation of the product as in Example 1 yielded the title product, with the same n.m.r. data as in Example 1.

We claim:

1. A process for preparing 1,3-(dihydroxy)-4-(acetylor propionyl)benzene, which comprises combining resorcinol with a) acetic acid or propionic acid, respectively, and b) hydrobromic acid at a temperature between about the boiling point of the reaction mixture to about 75° C. for between about one hour to about five days.

2. A process of claim 1, wherein 1,3-dihydroxy-4-acetylbenzene is prepared by combining resorcinol with acetic acid and hydrobromic acid at a temperature between about the boiling point of the reaction mixture to about 75° C. for between about one hour to about five days.

3. A process of claim 2, wherein the temperature is from between about 80° C. and about 90° C.

4. A process of claim 3, wherein the reaction mixture contains hydrogen bromide gas that has been dissolved in the glacial acetic acid.

* * * * *